(12) United States Patent
Lozier et al.

(10) Patent No.: US 9,113,916 B2
(45) Date of Patent: Aug. 25, 2015

(54) DRILL BIT FOR OSTEOCHONDRAL DRILLING WITH GUIDING ELEMENT AND USES THEREOF

(75) Inventors: Antony J Lozier, Warsaw, IN (US); Daniel P. Murphy, Claypool, IN (US); Andrew L. Gray, Warren, IN (US)

(73) Assignee: Zimmer, Inc., Warsaw, IN (US)

( * ) Notice: Subject to any disclaimer, the term of this patent is extended or adjusted under 35 U.S.C. 154(b) by 308 days.

(21) Appl. No.: 12/873,030

(22) Filed: Aug. 31, 2010

(65) Prior Publication Data

US 2012/0053588 A1 Mar. 1, 2012

(51) Int. Cl.
*A61B 17/16* (2006.01)
*A61B 19/00* (2006.01)

(52) U.S. Cl.
CPC ....... *A61B 17/1615* (2013.01); *A61B 2019/303* (2013.01); *Y10T 408/21* (2015.01); *Y10T 408/901* (2015.01); *Y10T 408/902* (2015.01); *Y10T 408/99* (2015.01)

(58) Field of Classification Search
CPC ................................................. B23B 2251/48
USPC ................... 606/79, 80, 81, 83, 96, 172, 180; 408/214, 220, 227, 230, 127, 202, 408/241 S, 226, 228
See application file for complete search history.

(56) References Cited

U.S. PATENT DOCUMENTS

| | | | |
|---|---|---|---|
| 1,405,720 A | 2/1922 | Scott | |
| 1,567,910 A | 12/1925 | Brynda et al. | |
| 1,703,154 A | 2/1929 | Lanzkron | |
| 1,842,573 A | 1/1932 | Van Treek | |
| 1,984,839 A * | 12/1934 | Murray | 116/200 |
| 3,564,947 A * | 2/1971 | Maier | 408/211 |
| 3,564,948 A | 2/1971 | Pomernacki | |
| 3,848,601 A | 11/1974 | Ma et al. | |
| 3,971,273 A | 7/1976 | Peters et al. | |
| 4,010,737 A | 3/1977 | Vilaghy et al. | |
| 4,250,892 A | 2/1981 | Dolhay et al. | |
| 4,589,206 A | 5/1986 | Marcoux | |

(Continued)

FOREIGN PATENT DOCUMENTS

| | | |
|---|---|---|
| AU | 4922296 A | 9/1996 |
| DE | 2411618 A1 | 4/1975 |

(Continued)

OTHER PUBLICATIONS

Fred H. Albee, Bone Surgery With Machine Tools, Apr. 1936, Scientific American, vol. 154.4, 178-181.*

(Continued)

*Primary Examiner* — Anu Ramana
*Assistant Examiner* — Jessica Weiss
(74) *Attorney, Agent, or Firm* — Schwegman Lundberg & Woessner, P.A.

(57) ABSTRACT

Drill bits comprising a shaft having a proximal end, a distal end, and a longitudinal axis extending between the proximal end and the distal end; and a cutting head located at the distal end of the shaft, having a cutting diameter, and having at least one flute, which includes a cutting edge and an offset leading spur are disclosed. A portion of the shaft of the drill bits located adjacent and proximal to the cutting head has a reduced diameter relative to the remainder of the shaft. The drill bits have a tapered point along the longitudinal axis at the distal end of the cutting head for guiding the drill bit or are cannulated to receive a guide wire.

21 Claims, 5 Drawing Sheets

(56) References Cited

U.S. PATENT DOCUMENTS

| | | | |
|---|---|---|---|
| 4,706,659 A * | 11/1987 | Matthews et al. | 606/80 |
| 5,067,964 A | 11/1991 | Richmond et al. | |
| 5,115,704 A | 5/1992 | Hyman | |
| 5,139,520 A | 8/1992 | Rosenberg | |
| 5,152,791 A | 10/1992 | Hakamatsuka et al. | |
| 5,184,926 A * | 2/1993 | Hemmings | 408/226 |
| 5,197,833 A * | 3/1993 | Mayer et al. | 408/226 |
| 5,328,722 A | 7/1994 | Ghanayem et al. | |
| 5,341,816 A | 8/1994 | Allen | |
| 5,362,166 A | 11/1994 | Yamamoto et al. | |
| 5,368,051 A | 11/1994 | Dunn et al. | |
| 5,370,692 A | 12/1994 | Fink et al. | |
| 5,423,823 A | 6/1995 | Schmieding | |
| 5,425,490 A | 6/1995 | Goble et al. | |
| 5,443,468 A | 8/1995 | Johnson | |
| 5,575,798 A | 11/1996 | Koutrouvelis | |
| 5,591,234 A | 1/1997 | Kirsch | |
| 5,632,745 A * | 5/1997 | Schwartz | 606/75 |
| 5,632,747 A | 5/1997 | Scarborough et al. | |
| 5,718,707 A | 2/1998 | Mikhail | |
| 5,788,713 A | 8/1998 | Dubach et al. | |
| 5,810,887 A | 9/1998 | Accorti, Jr. et al. | |
| 5,860,946 A | 1/1999 | Hofstatter | |
| 5,876,452 A | 3/1999 | Athanasiou et al. | |
| 5,899,860 A | 5/1999 | Pfeiffer et al. | |
| 5,904,717 A | 5/1999 | Brekke et al. | |
| 5,919,196 A | 7/1999 | Bobic et al. | |
| 5,921,987 A | 7/1999 | Stone | |
| 6,110,178 A | 8/2000 | Zech et al. | |
| 6,231,608 B1 | 5/2001 | Stone | |
| 6,242,247 B1 | 6/2001 | Rieser et al. | |
| 6,251,143 B1 | 6/2001 | Schwartz et al. | |
| 6,270,503 B1 | 8/2001 | Schmieding | |
| 6,306,142 B1 | 10/2001 | Johanson et al. | |
| 6,354,774 B1 * | 3/2002 | Haughton et al. | 408/225 |
| 6,358,253 B1 | 3/2002 | Torrie et al. | |
| 6,375,658 B1 | 4/2002 | Hangody et al. | |
| 6,395,011 B1 | 5/2002 | Johanson et al. | |
| 6,439,811 B1 * | 8/2002 | Wardell | 407/54 |
| 6,488,033 B1 | 12/2002 | Cerundolo | |
| 6,530,928 B1 | 3/2003 | Frei et al. | |
| 6,582,438 B2 | 6/2003 | DeMayo | |
| 6,591,581 B2 | 7/2003 | Schmieding | |
| 6,592,588 B1 | 7/2003 | Bobic et al. | |
| 6,656,195 B2 * | 12/2003 | Peters et al. | 606/159 |
| 6,767,354 B2 | 7/2004 | Johanson et al. | |
| 6,793,429 B2 | 9/2004 | Arrison | |
| 6,852,114 B2 | 2/2005 | Cerundolo | |
| 6,858,042 B2 | 2/2005 | Nadler | |
| 6,988,015 B1 | 1/2006 | Schopf et al. | |
| 6,998,418 B1 | 2/2006 | Sung et al. | |
| 7,048,477 B2 * | 5/2006 | Abrams | 408/1 R |
| 7,160,305 B2 | 1/2007 | Schmieding | |
| 7,264,634 B2 | 9/2007 | Schmieding | |
| 7,371,260 B2 | 5/2008 | Malinin | |
| 7,416,371 B2 * | 8/2008 | Scott et al. | 408/1 R |
| 7,548,865 B2 | 6/2009 | Schmieding | |
| 7,550,007 B2 | 6/2009 | Malinin | |
| 7,563,266 B2 | 7/2009 | Camino et al. | |
| 7,572,291 B2 | 8/2009 | Gil et al. | |
| 7,591,820 B2 | 9/2009 | Schmieding et al. | |
| 7,608,098 B1 | 10/2009 | Stone et al. | |
| 7,666,230 B2 | 2/2010 | Orban et al. | |
| 7,758,583 B2 | 7/2010 | Gil et al. | |
| 7,758,643 B2 | 7/2010 | Stone et al. | |
| 7,776,043 B2 | 8/2010 | Hycz et al. | |
| 7,833,269 B2 | 11/2010 | Nycz et al. | |
| 7,862,567 B2 | 1/2011 | Schmieding | |
| 7,875,032 B2 | 1/2011 | Lyons | |
| 7,879,040 B2 | 2/2011 | Bharadwaj | |
| 7,887,546 B2 | 2/2011 | Gil et al. | |
| 7,905,904 B2 | 3/2011 | Stone et al. | |
| 7,909,851 B2 | 3/2011 | Stone et al. | |
| 7,909,873 B2 | 3/2011 | Tan-Malecki et al. | |
| 7,914,539 B2 | 3/2011 | Stone et al. | |
| 7,955,335 B2 | 6/2011 | Gil et al. | |
| 7,955,336 B2 | 6/2011 | Gil et al. | |
| 7,985,230 B2 | 7/2011 | Gil et al. | |
| 7,997,174 B2 | 8/2011 | Gil et al. | |
| 8,034,090 B2 | 10/2011 | Stone et al. | |
| 8,048,079 B2 | 11/2011 | Iannarone | |
| RE43,714 E | 10/2012 | Nadler et al. | |
| 8,435,305 B2 | 5/2013 | Lozier et al. | |
| 8,753,406 B2 | 6/2014 | Lozier et al. | |
| 8,801,725 B2 | 8/2014 | Ritter et al. | |
| 2003/0167062 A1 | 9/2003 | Gambale et al. | |
| 2003/0171810 A1 | 9/2003 | Steiner | |
| 2004/0039400 A1 | 2/2004 | Schmieding et al. | |
| 2004/0193154 A1 | 9/2004 | Leatherbury et al. | |
| 2004/0230194 A1 | 11/2004 | Urbanski et al. | |
| 2005/0013872 A1 | 1/2005 | Freyman | |
| 2005/0021044 A1 | 1/2005 | Stone et al. | |
| 2005/0038520 A1 | 2/2005 | Binette et al. | |
| 2005/0080435 A1 | 4/2005 | Smith et al. | |
| 2005/0137600 A1 * | 6/2005 | Jacobs et al. | 606/79 |
| 2006/0131906 A1 | 6/2006 | Maurer et al. | |
| 2006/0247790 A1 | 11/2006 | McKay | |
| 2007/0043376 A1 | 2/2007 | Leatherbury et al. | |
| 2007/0135917 A1 | 6/2007 | Malinin | |
| 2007/0135918 A1 | 6/2007 | Malinin | |
| 2007/0149982 A1 | 6/2007 | Lyons | |
| 2007/0270711 A1 | 11/2007 | Gil et al. | |
| 2008/0051812 A1 | 2/2008 | Schmitz et al. | |
| 2008/0095588 A1 * | 4/2008 | Henderer et al. | 408/222 |
| 2008/0138165 A1 * | 6/2008 | Durfee | 408/230 |
| 2008/0167653 A1 * | 7/2008 | Watlington et al. | 606/81 |
| 2008/0195115 A1 | 8/2008 | Oren et al. | |
| 2008/0200915 A1 | 8/2008 | Globerman et al. | |
| 2008/0243028 A1 | 10/2008 | Howard et al. | |
| 2008/0243029 A1 | 10/2008 | Howard et al. | |
| 2008/0255427 A1 | 10/2008 | Satake et al. | |
| 2008/0262616 A1 | 10/2008 | McKay | |
| 2008/0269566 A1 | 10/2008 | Measamer et al. | |
| 2008/0306608 A1 | 12/2008 | Nycz et al. | |
| 2009/0024224 A1 | 1/2009 | Chen et al. | |
| 2009/0047085 A1 * | 2/2009 | Liao et al. | 408/230 |
| 2009/0054906 A1 | 2/2009 | Walthall et al. | |
| 2009/0076556 A1 | 3/2009 | Mcgarity et al. | |
| 2009/0080989 A1 * | 3/2009 | Dost et al. | 408/225 |
| 2009/0171359 A1 | 7/2009 | Sterrett | |
| 2009/0209962 A1 | 8/2009 | Jamali | |
| 2009/0275950 A1 | 11/2009 | Sterrett et al. | |
| 2009/0281550 A1 | 11/2009 | Keller | |
| 2009/0299371 A1 | 12/2009 | Steiner et al. | |
| 2009/0299372 A1 | 12/2009 | Steiner et al. | |
| 2009/0319051 A9 | 12/2009 | Nycz et al. | |
| 2010/0123325 A1 | 5/2010 | Maffeis | |
| 2010/0168750 A1 | 7/2010 | Sherman | |
| 2010/0249786 A1 | 9/2010 | Schmieding et al. | |
| 2010/0292704 A1 | 11/2010 | Stoffel et al. | |
| 2011/0009872 A1 | 1/2011 | Mistry et al. | |
| 2011/0046628 A1 | 2/2011 | Jamali | |
| 2011/0054408 A1 | 3/2011 | Wei et al. | |
| 2011/0137315 A1 | 6/2011 | Gil et al. | |
| 2011/0144648 A1 | 6/2011 | Gil et al. | |
| 2011/0208193 A1 | 8/2011 | Gil et al. | |
| 2012/0053642 A1 | 3/2012 | Lozier et al. | |
| 2012/0150030 A1 | 6/2012 | Reach, Jr. et al. | |
| 2013/0231745 A1 | 9/2013 | Lozier et al. | |

FOREIGN PATENT DOCUMENTS

| | | |
|---|---|---|
| DE | 2830566 A1 | 1/1980 |
| DE | 2933174 A1 | 4/1980 |
| DE | 4317448 A1 | 11/1994 |
| DE | 19503504 A1 | 3/1996 |
| EP | 0307241 A2 | 3/1989 |
| EP | 0493698 A1 | 7/1992 |
| EP | 0508710 A1 | 10/1992 |
| EP | 0768332 A1 | 4/1997 |
| EP | 0815809 A2 | 1/1998 |
| EP | 0824893 A2 | 2/1998 |
| FR | 2700462 A1 | 7/1994 |
| GB | 2175506 A | 12/1986 |

(56) References Cited

FOREIGN PATENT DOCUMENTS

| | | |
|---|---|---|
| JP | 3178652 A | 2/1991 |
| JP | 4303450 A | 10/1992 |
| JP | 9122226 A | 5/1997 |
| JP | 10251492 A | 9/1998 |
| JP | 10513386 A | 12/1998 |
| WO | WO-9315694 A1 | 8/1993 |
| WO | WO-9426211 A1 | 11/1994 |
| WO | WO-9624302 A1 | 8/1996 |
| WO | WO-9624310 A1 | 8/1996 |
| WO | WO-9627333 A1 | 9/1996 |
| WO | WO-9725942 A1 | 7/1997 |
| WO | WO-9746665 A1 | 12/1997 |
| WO | WO-9834569 A1 | 8/1998 |
| WO | WO-9834596 A2 | 8/1998 |
| WO | WO-9840027 A1 | 9/1998 |
| WO | WO-9856317 A1 | 12/1998 |
| WO | WO-0143667 A1 | 6/2001 |
| WO | WO-0224244 A2 | 3/2002 |
| WO | WO-2005023321 A2 | 3/2005 |
| WO | WO-2005094694 A2 | 10/2005 |
| WO | WO-2006026325 A2 | 3/2006 |
| WO | WO-2008/147692 A1 | 12/2008 |
| WO | WO-2010092100 A1 | 8/2010 |
| WO | WO-2011008968 A1 | 1/2011 |

OTHER PUBLICATIONS

"U.S. Appl. No. 12/045,416, Response filed Jul. 17, 2012 to Final Office Action mailed Feb. 17, 2012", 19 pgs.
"U.S. Appl. No. 12/873,049, Restriction Requirement mailed Jul. 10, 2012", 5 pgs.
"U.S. Appl. No. 11/705,575, Notice of Allowance mailed May 15, 2012", 5 pgs.
"U.S. Appl. No. 11/705,575, Response filed Dec. 15, 2011 to Non Final Office Action mailed Sep. 15, 2011", 14 pgs.
"U.S. Appl. No. 12/045,416, Final Office Action mailed Feb. 17, 2012", 13 pgs.
"U.S. Appl. No. 12/045,416, Response filed Dec. 5, 2011 to Non Final Office Action mailed Aug. 4, 2011", 18 pgs.
"U.S. Appl. No. 12/196,831, Advisory Action mailed Jul. 5, 2012", 3 pgs.
"U.S. Appl. No. 12/196,831, Examiner Interview Summary mailed Feb. 6, 2012", 18 pgs.
"U.S. Appl. No. 12/196,831, Final Office Action mailed Apr. 12, 2012", 17 pgs.
"U.S. Appl. No. 12/196,831, Response filed Feb. 1, 2012 to Non Final Office Action mailed Oct. 6, 2011", 15 pgs.
"U.S. Appl. No. 12/196,831, Response filed Jun. 6, 2012 to Final Office Action mailed Apr. 12, 2012", 14 pgs.
"U.S. Appl. No. 12/196,831, Response filed Sep. 12, 2012 to Advisory Action mailed Jul. 5, 2012", 16 pgs.
"U.S. Appl. No. 12/873,049, Response filed Jul. 27, 2012 to Restriction Requirement mailed Jul. 10, 2012", 8 pgs.
Bobic, V, "Arthroscopic osteochondral autograft transplantation in anterior cruciate ligament reconstruction: a preliminary clinical study", Knee Surg, Sport Traumatol, Arthroscopy 3, (1996), 262-264.
Convery, F.R., et al., "The Repair of Large Osteochondral Defects", An Experimental Study in Horses, Clin. Orthrop. 82., (1972), 253-262.
Ehalt, Walther M, "Grafting of joint-cartilage Bone-Blocks from the bank", VI. Congr. Soc. Internat. Chir. Orthop. Traumatol. S., (1954), 419-421.
Garrett, John C, "Treatment of Osteochondral Defects of the Distal Femur with Fresh Osteochondral Allografts: A Preliminary Report", Arthroscopy: The Journal of Arthroscopic and Related Surgery 2(4), (1986), 222-226.
Guhl, James F, "Chapter 21: The Impact of Arthroscopy on Osteochondritis Dissecans", Operative Arthroscopy, (1991), 297-317.

Hangody, L., et al., "Autogenous osteochondral grafting in the knees of German Shepherd dogs: Radiographic and histological analysis", Hungarian Review of Sports Medicine 35, (1994), 117-123.
Hangody, L., et al., "Treatment of localized chondral and osteochondral defects in the knee by a new autogenous osteochondral grafting tenique", Hungarian Review of Sports Medicine 35, (1994), 241-246.
Hangody, Laszlo, "Arthroscopic autogeous osteochondral mosaicplasty for the treatment of femoral condylar articular defects: A preliminary report", Knee Surg, Sports Traumatol, Arthrosc 5, (1997), 262-267.
Hangody, Laszlo, "Autologous osteochondral mosaic-like graft technique for replacing weight bearing cartilage defects", 7th Congress of ESSTKSA, Abstract Only, (1996), 3 pgs.
Hangody, Laszlo, et al., "Autologous Osteochondral Mosaic-Plasty", Review of Osteology 3, (1996), 70-73.
Hangody, Laszlo, "Chapter 13: Autogenous Osteochondral Mosaicplasty for the Treatment of Focal Chondral and Osteochondral Defects of the Femoral Condyles", Knieinstabilitat und Knorpelschaden, (1998), 97-106.
Hangody, Laszlo, "Mosaic-plasty in Clinical Practice", Review of Osteology 4, (1996), 32-36.
Hangody, Laszlo, et al., "Mosaicplasty for the Treatment of Articular Cartilage Defects: Application in Clinical Practice", Orthopedics 21(2), (1998), 751-756.
Hangody, Laszlo, et al., "Mosaicplasty for the treatment of osteochondritis dissecans of the knee", [Online]. Retrieved from the Internet: <URL: http://www.egydoc.com/Sites/Arthroclub/AC_Files/Articles/article39.pdf>, (Accessed Nov. 8, 2005), 9 pgs.
Hangody, Laszlo, et al., "New Method in Treatment of Sever Local Cartilage Damage in the Knee Joint (Eine neue Methode in der Behandlung von schweren, lokalen Knorpelschaden im Kniegelenk", Osteosynthese International 5, (1997), 316-321.
Hangody, Laszlo, et al., "Osteochondral Plugs: Autogenous Osteochondral Mosaicplasty for the Treatment of Focal Chondral and Osteochondral Articular Defects", Operative Techniques in Orthopaedics 7(4), (1997), 312-322.
Hangody, Laszlo, et al., "Treatment of Osteochondritis Dissecans of the Talus: Use of Mosaicplasty Technique—A Preliminary Report", Foot and Ankle International 18(10), (1997), 628-634.
Lindholm, Sam, et al., "Reconstruction of the Articular Surface by Transfixation of an Osteochondral Fragment of the Femoral Condyle Using a Bone Transplant", Scandinavian Journal of Rheumatology Supplement 44, (1982), 5-13.
Muller, W, "Osteochondrosis Dissecans", Progress in Orthopaedic Surgery vol. 3, (1978), 135-142.
Woods, T, "Effectiveness of three extraction techniques in the development of a decellularized bone-anterior cruciate ligament-bone graft", Biomaterials, Elsevier Science Publishers BV., Barking, GB, vol. 26, No. 35, (Dec. 1, 2005), 7339-7349.
Yamashita, et al., "The Transplantation of an Autogeneic Osteochondral Fragment for Osteochondritis Dissecans of the Knee", Clinical Orthopaedics and Related Research, No. 201, (1985), 43-50.
"U.S. Appl. No. 10/149,853, Non Final Office Action mailed Apr. 13, 2004", 8 pgs.
"U.S. Appl. No. 10/149,853, Notice of Allowance mailed Oct. 5, 2004", 7 pgs.
"U.S. Appl. No. 10/149,853, Preliminary Amendment filed Oct. 17, 2002", 6 pgs.
"U.S. Appl. No. 10/149,853, Response filed Jul. 6, 2004 to Non Final Office Action mailed Apr. 13, 2004", 9 pgs.
"U.S. Appl. No. 11/705,575, Non Final Office Action mailed Mar. 16, 2005", 9 pgs.
"U.S. Appl. No. 11/705,575, Non Final Office Action mailed Sep. 15, 2011", 8 pgs.
"U.S. Appl. No. 11/705,575, Notice of Non-Compliant Amendment mailed Jan. 7, 2011", 3 pgs.
"U.S. Appl. No. 11/705,575, Notice of Non-Compliant Amendment mailed Oct. 29, 2010", 3 pgs.
"U.S. Appl. No. 11/705,575, Preliminary Amendment filed Feb. 12, 2007", 14 pgs.

(56) References Cited

OTHER PUBLICATIONS

"U.S. Appl. No. 11/705,575, Response filed Feb. 7, 2011 to Notice of Non-Compliant Amendment mailed Jan. 7, 2011", 22 pgs.
"U.S. Appl. No. 11/705,575, Response filed Sep. 15, 2010 to Non Final Office Action mailed Mar. 16, 2010", 13 pgs.
"U.S. Appl. No. 11/705,575, Response filed Nov. 29, 2010 to Notice of Non-Compliant Amendment mailed Oct. 29, 2010", 14 pgs.
"U.S. Appl. No. 11/705,575, Revised Preliminary Amendment filed Sep. 15, 2010 in Response to Office Action mailed Mar. 16, 2010", 11 pgs.
"U.S. Appl. No. 11/753,102, Advisory Action filed Dec. 10, 2010", 3 pgs.
"U.S. Appl. No. 11/753,102, Final Office Action mailed Aug. 3, 2010", 15 pgs.
"U.S. Appl. No. 11/753,102, Non Final Office Action mailed Jan. 4, 2010", 23 pgs.
"U.S. Appl. No. 11/753,102, Response filed May 4, 2010 to Non Final Office Action mailed Jan. 4, 2010", 13 pgs.
"U.S. Appl. No. 11/753,102, Response filed Nov. 23, 2009 to Restriction Requirement mailed Oct. 30, 2009", 12 pgs.
"U.S. Appl. No. 11/753,102, Response filed Dec. 3, 2010 to Final Office Action mailed Aug. 3, 2010", 15 pgs.
"U.S. Appl. No. 11/753,102, Restriction Requirement mailed Oct. 30, 2009", 9 pgs.
"U.S. Appl. No. 11/759,679, Final Office Action mailed Oct. 7, 2010", 17 pgs.
"U.S. Appl. No. 11/759,679, Non Final Office Action mailed Feb. 26, 2010", 14 pgs.
"U.S. Appl. No. 11/759,679, Response filed Jun. 28, 2009 to Non Final Office Action mailed Feb. 26, 2010", 13 pgs.
"U.S. Appl. No. 11/759,679, Response filed Oct. 30, 2009 to Restriction Requirement mailed Sep. 4, 2009", 3 pgs.
"U.S. Appl. No. 11/759,679, Restriction Requirement mailed Sep. 4, 2009", 6 pgs.
"U.S. Appl. No. 12/045,416, Non Final Office Action mailed Aug. 4, 2011", 12 pgs.
"U.S. Appl. No. 12/045,416, Response filed Jun. 2, 2011 to Restriction Requirement mailed May 11, 2011", 13 pgs.
"U.S. Appl. No. 12/045,416, Restriction Requirement mailed May 11, 2011", 8 pgs.
"U.S. Appl. No. 12/196,831, Advisory Action mailed Jan. 21, 2011", 3 pgs.
"U.S. Appl. No. 12/196,831, Final Office Action mailed Nov. 12, 2010", 10 pgs.
"U.S. Appl. No. 12/196,831, Non Final Office Action mailed Jul. 9, 2010", 7 pgs.
"U.S. Appl. No. 12/196,831, Non Final Office Action mailed Oct. 6, 2011", 8 pgs.
"U.S. Appl. No. 12/196,831, Response filed Jan. 10, 2011 to Final Office Action mailed Nov. 12, 2010", 10 pgs.
"U.S. Appl. No. 12/196,831, Response filed Jun. 21, 2010 to Restriction Requirement mailed Jun. 8, 2010", 8 pgs.
"U.S. Appl. No. 12/196,831, Response filed Oct. 7, 2010 to Non Final Office Action mailed Jul. 9, 2010", 11 pgs.
"U.S. Appl. No. 12/196,831, Restriction Requirement mailed Jun. 8, 2010", 7 pgs.
"International Application Serial No. PCT/US2008/063582, International Search Report mailed Oct. 9, 2008", 3 pgs.
"International Application Serial No. PCT/US2008/063582, Written Opinion mailed Oct. 9, 2008", 7 pgs.
"International Application Serial No. PCT/US2008/064653, International Search Report mailed Sep. 7, 2009", 5 pgs.
"International Application Serial No. PCT/US2008/064653, Written Opinion mailed Sep. 7, 2009", 8 pgs.
"International Application Serial No. PCT/US2009/036661, International Search Report mailed Jun. 12, 2009", 4 pgs.
"International Application Serial No. PCT/US2009/036661, Written Opinion mailed Jun. 12, 2009", 8 pgs.
Garrett, J. C., "Chapter 34—Osteochondral Allografts", 355-358.
"Australian Application Serial No. 200116857, Office Action mailed Feb. 13, 2004", 2 pgs.
"Canadian Application Serial No. 00979315.9, Office Action mailed Jan. 24, 2007", 3 pgs.
"Canadian Application Serial No. 00979315.9, Response filed Jul. 23, 2007 to Office Action mailed Jan. 24, 2007", 14 pgs.
"European Application Serial No. 04020622.9, European Search Report mailed Nov. 29, 2004", 6 pgs.
"European Application Serial No. 04020622.9, Office Action mailed Oct. 20, 2005", 3 pgs.
"European Application Serial No. 04020622.9, Response filed Apr. 13, 2006 to Office Action mailed Oct. 20, 2005", 12 pgs.
"International Application Serial No. PCT/CH00/00659, International Preliminary Examination Report mailed Mar. 20, 2002", 15 pgs.
"International Application Serial No. PCT/CH00/00659, International Search Report mailed Jan. 2, 2001", 8 pgs.
"International Application Serial No. PCT/US2008/063582, International Preliminary Report on Patentability mailed Nov. 24, 2009", 8 pgs.
"International Application Serial No. PCT/US2009/036661, International Preliminary Report on Patentability mailed Sep. 14, 2010", 9 pgs.
"Japanese Application Serial No. 2000-544609, Office Action mailed Jan. 5, 2010", 9 pgs.
"Japanese Application Serial No. 2000-544609, Office Action mailed Mar. 24, 2009", 8 pgs.
"Japanese Application Serial No. 2000-544609, Office Action mailed Aug. 5, 2008", 5 pgs.
"Japanese Application Serial No. 2000-544609, Office Action mailed Nov. 2, 2010", 7 pgs.
"Japanese Application Serial No. 2000-544609, Response filed Apr. 27, 2010 to Office Action mailed Jan. 24, 2010", 8 pgs.
"Japanese Application Serial No. 2000-544609, Response filed Jun. 11, 2009 to Office Action mailed Mar. 24, 2009", 14 pgs.
"Japanese Application Serial No. 2000-544609, Response filed Oct. 28, 2008 to Office Action mailed Aug. 5, 2008", 14 pgs.
"U.S. Appl. No. 12/873,049, Notice of Allowance mailed Nov. 14, 2012", 13 pgs.
"U.S. Appl. No. 12/196,831, Non Final Office Action mailed Oct. 3, 2013", 21 pgs.
"U.S. Appl. No. 12/873,049, Notice of Allowance mailed Mar. 25, 2013", 9 pgs.
"U.S. Appl. No. 13/619,022, Non Final Office Action mailed May 8, 2013", 6 pgs.
"U.S. Appl. No. 13/855,157, Non Final Office Action mailed Oct. 10, 2013", 15 pgs.
"U.S. Appl. No. 10/149,853, Preliminary Amendment filed Sep. 14, 2012", 7 pgs.
"U.S. Appl. No. 11/753,102, Non Final Office Action mailed Feb. 26, 2014", 9 pgs.
"U.S. Appl. No. 12/196,831, Examiner Interview Summary mailed Nov. 25, 2013", 3 pgs.
"U.S. Appl. No. 12/196,831, Final Office Action mailed Jan. 30, 2014", 19 pgs.
"U.S. Appl. No. 12/196,831, Response filed Nov. 27, 2013 to Non-Final Office Action dated Oct. 3, 2013", 13 pgs.
"U.S. Appl. No. 13/855,157, Notice of Allowance mailed Feb. 11, 2014", 10 pgs.
"U.S. Appl. No. 13/855,157, Preliminary Amendment filed Apr. 5, 2013", 7 pgs.
"U.S. Appl. No. 13/855,157, Response filed Jan. 10, 2014 to Non-Final Office Action dated Oct. 10, 2013", 8 pgs.
"International Application Serial No. PCT/US2008/064653, International Preliminary Report on Patentability mailed", 9 pgs.
"U.S. Appl. No. 11/753,102, Final Office Action mailed Sep. 9, 2014", 9 pgs.
"U.S. Appl. No. 11/753,102, Response filed May 27, 2014 to Non-Final Office Action mailed Feb. 26, 2014", 8 pgs.
"U.S. Appl. No. 12/045,416, Notice of Allowance mailed May 9, 2014", 14 pgs.

\* cited by examiner

DRILL BIT FOR OSTEOCHONDRAL DRILLING WITH GUIDING ELEMENT AND USES THEREOF

BACKGROUND

The present invention relates to devices for developing a bore in bone tissue and, more particularly, to drill bits for creating a hole in a selected osteochondral site. The invention also relates to the use of the drill bits to create a hole in a selected osteochondral site.

The drill bit of the present invention can also be used or adapted for use with other tissue surfaces having components of varying hardness, (e.g., periosteum, bone, cartilage and/or other attached elastic materials).

Articular cartilage, especially of the hips, knees, shoulder, and ankle, are subject to high wear rates over time, which may cause degradation of cartilage tissue. Trauma along with disease, are also players contributing to the damage and degeneration of articular cartilage. To repair these defect sites, typically, a cylindrical hole of a desired diameter (or holes, potentially, depending on the size of the defect) is formed at the site of the damage. The holes have in the past been formed using instruments such as punches, twist drill bits, end mill style bits, and reamers. The excised hole is then filled with a replacement graft, either biological or synthetic, having a diameter generally corresponding to the diameter of the hole.

As indicated, the use of drill bits for the creation of holes in osteochondral tissue is known. However, problems can occur with existing osteochondral drill bits when drilling through bone and cartilage. The properties of the overlaying cartilage, subchondral bone, and trabecular bone all must be considered to ensure a clean well cut hole. The toughness and elasticity of cartilage and the extremely hard subchondral bone makes drilling/reaming/punching a clean, well-cut hole at the desired location difficult. The open-celled structure of trabecular bone is prone to crushing and/or undesired chipping with the advancement of instruments. When drilling, it has been known for drill bits to create a ragged, unclean, imprecise hole as well as to impose trauma to surrounding tissue.

Particularly large defects sites, requiring larger instrumentation, may further amplify these problems. Impacting a large diameter punch into an osteochondral site spreads the force over a large area. Spreading the concentration of this force over the large area increases the puncture force required for penetration. This can cause unwanted fracturing of the subchondral bone, as well as, rolling of the cartilage over the lip around the hole wall.

Thus, there exists a need for improved instrumentation that overcomes these limitations.

SUMMARY

The present invention relates to devices for developing a bore in bone tissue and, more particularly, to drill bits for creating a hole in a selected osteochondral site. The invention also relates to the use of the drill bits to create a hole in a selected osteochondral site.

The drill bit of the present invention can also be used or adapted for use with other tissue surfaces having components of varying hardness, (e.g., periosteum, bone, cartilage and/or other attached elastic materials).

According to a first aspect of the present invention, there is a drill bit comprising: a shaft having a proximal end, a distal end, and a longitudinal axis extending between the proximal end and the distal end, a cutting: head located at the distal end of the shaft, having a cutting diameter, and having at least one flute, which includes a cutting edge and an offset leading spur, a tapered point located along the longitudinal axis at a distal end of the cutting head for guiding the drill bit, and wherein a portion of the shaft located adjacent and proximal to the cutting head has a reduced diameter relative to the remainder of the shaft.

The tapered point may be threaded. Also, the shaft may be flexible. The drill bit may further comprise a depth controlling element. The depth controlling element may comprise one or more visual markings located on the cutting head, a mechanical stop located proximal to the cutting head, or a combination thereof. The one or more visual markings may be etched into the cutting head. The mechanical stop may be fixed or removable. Additionally, the drill bit may comprise a marking indicating the cutting diameter of the cutting head. The marking indicating the cutting diameter of the cutting head may comprise a colored band located on a mechanical stop that is located proximal to the cutting head.

In accordance with another aspect of the present invention, there is provided a method for creating a hole in a selected osteochondral site using a drill bit. The drill bit comprises a shaft having a proximal end, a distal end, and a longitudinal axis extending between the proximal end and the distal end, a cutting head located at the distal end of the shaft, having a cutting diameter, and having at least one flute, which includes a cutting edge and an offset leading spur, a tapered point located along the longitudinal axis at a distal end of the cutting head for guiding the drill bit, and wherein a portion of the shaft located adjacent and proximal to the cutting head has a reduced diameter relative to the remainder of the shaft. The method comprises advancing the drill bit into the selected osteochondral site, contacting cartilage with the offset leading spur, contacting bone with the cutting edge, displacing cartilage and bone proximally, and collecting displaced cartilage and bone in the portion of the shaft having a reduced diameter relative to the remainder of the shaft.

The method may comprise using a tapered point of the drill bit to guide the path of the drill bit. The method may also comprise using a cannula to guide the path of the drill bit. The method may further comprise using the cannula and the portion of the shaft having a reduced diameter relative to the remainder of the shaft to contain bone and cartilage.

The method may also comprise using a depth controlling element to achieve a desired drilling depth. The depth controlling element may comprise one or more visual markings located on the cutting head, a mechanical stop located proximal to the cutting head, or a combination thereof.

In accordance with another embodiment of the invention, there is provided a drill bit comprising: a shaft having a proximal end, a distal end, a longitudinal axis extending between the proximal end and the distal end, and an internal bore extending along the longitudinal axis of the shaft adapted to receive a guide wire, a cutting head located at the distal end of the shaft, having a cutting diameter, and having at least one flute which includes a cutting edge and an offset leading spur, and wherein a portion of the shaft located adjacent and proximal to the cutting head has a reduced diameter relative to the remainder of the shaft.

The shaft may be flexible. The drill bit may also comprise a depth controlling element. The depth controlling element may comprise one or more visual markings located on the cutting head, mechanical stop located proximal to the cutting head, or a combination thereof. The one or more visual markings may be etched into the cutting head. The drill bit may further comprise a mechanical stop that is fixed or removable. The drill bit may further comprise a marking indicating the cutting diameter of the cutting head. The marking indicating the cutting diameter of the cutting head may comprise a colored band located on a mechanical stop that is located proximal to the cutting head.

In accordance with a further aspect of the present invention, there is provided a method for creating a hole in a selected osteochondral site using a drill bit. The drill bit comprises: a shaft having a proximal end, a distal end, a longitudinal axis extending between the proximal end and the distal end, and an internal bore extending along the longitudinal axis of the shaft adapted to receive a guide wire, a cutting head located at the distal end of the shaft, having a cutting diameter, and having at least one flute, which includes a cutting edge and an offset leading spur, a depth controlling element, and wherein a portion of the shaft located adjacent and proximal to the cutting head has a reduced diameter relative to the remainder of the shaft. The method comprises inserting a guide wire into a selected osteochondral site, advancing the drill bit over the guide wire, and contacting cartilage with the offset leading spur, contacting bone with the cutting edge, displacing cartilage and bone proximally, using the depth controlling element to achieve a desired drilling depth, and collecting displaced cartilage and bone in the portion of the shaft having a reduced diameter relative to the remainder of the shaft.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

The present invention relates to devices for developing a bore in bone tissue and, more particularly, to drill bits for creating a hole in a selected osteochondral site. The invention also relates to the use of the drill bits to create a hole in a selected osteochondral site.

The drill bit of the present invention can also be used or adapted for use with other tissue surfaces having components of varying hardness, (e.g., periosteum, bone, cartilage and/or other attached elastic materials).

The drill bits and the methods of creating holes using the drill bits of the present invention are advantageous because they provide a method for stabilizing and guiding the drill bit to the correct location while drilling to create a hole at a selected osteochondral site with clean, smooth walls and bottom. The drill bits of the present invention and methods of using them also result in the minimization of trauma to tissue surrounding the drilled hole. Particularly, the use of a drill bit with a tapered point at the distal end or the use of a drill bit with an internal bore for receiving a guide wire are particularly useful in stabilizing and guiding a drill bit.

In the descriptions of the components that follow, various preferences for materials of construction are generally expressed. Typically, instrument grade steel is employed for the disclosed drill bits. The use of other materials of construction for the components, beyond any expressed preferences, is within the scope of the present invention. Generally, any material of construction can be used for a component as long as the function of the component is not defeated and the material of construction is considered acceptable for a surgical environment.

Figure 1:
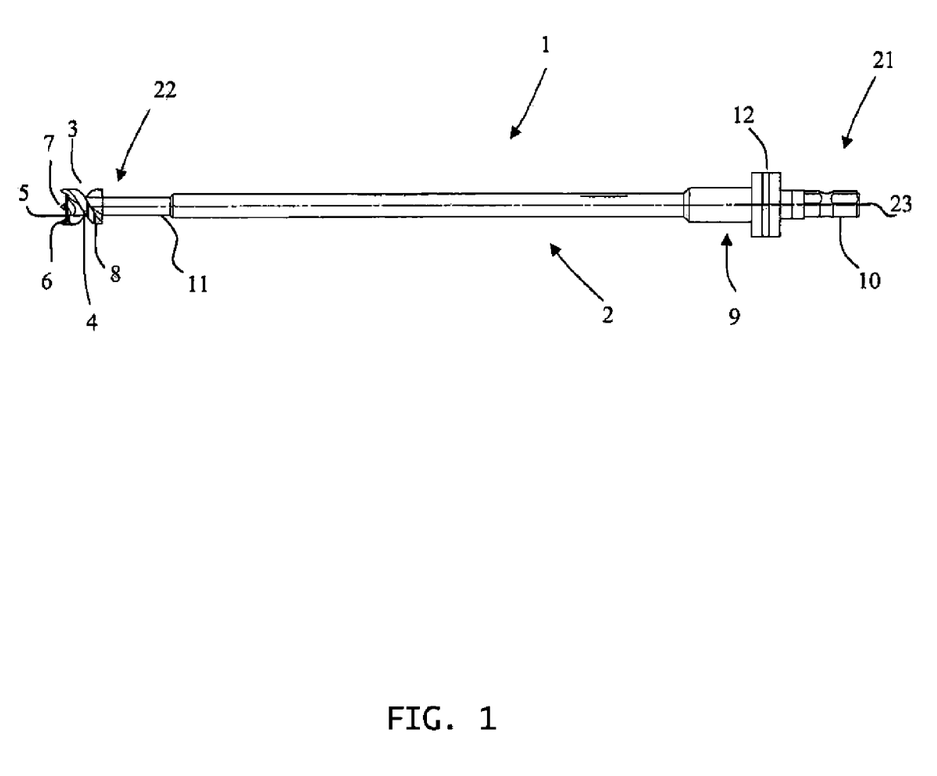
FIG. 1 is an elevational view showing a drill of the present invention with a non-threaded tapered point.
Figure 2:
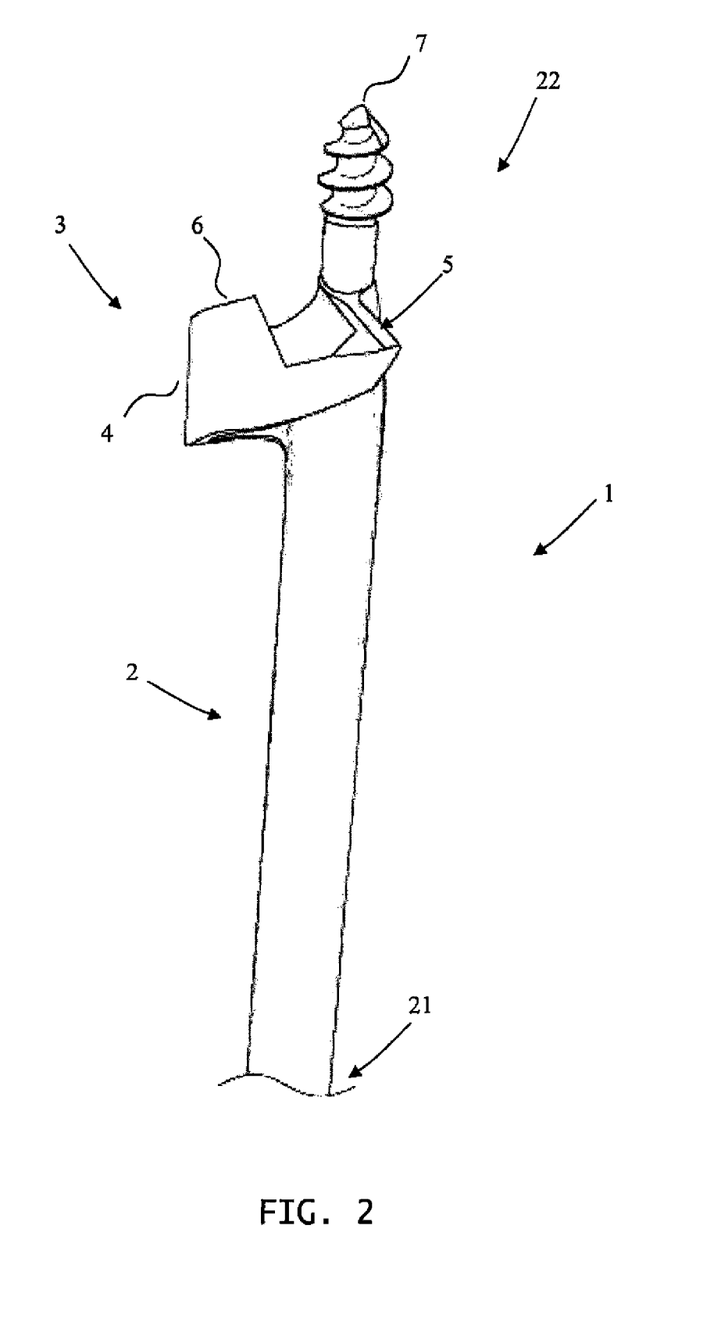
FIG. 2 is an elevational view showing a drill of the present invention with a threaded tapered point.
Figure 4:
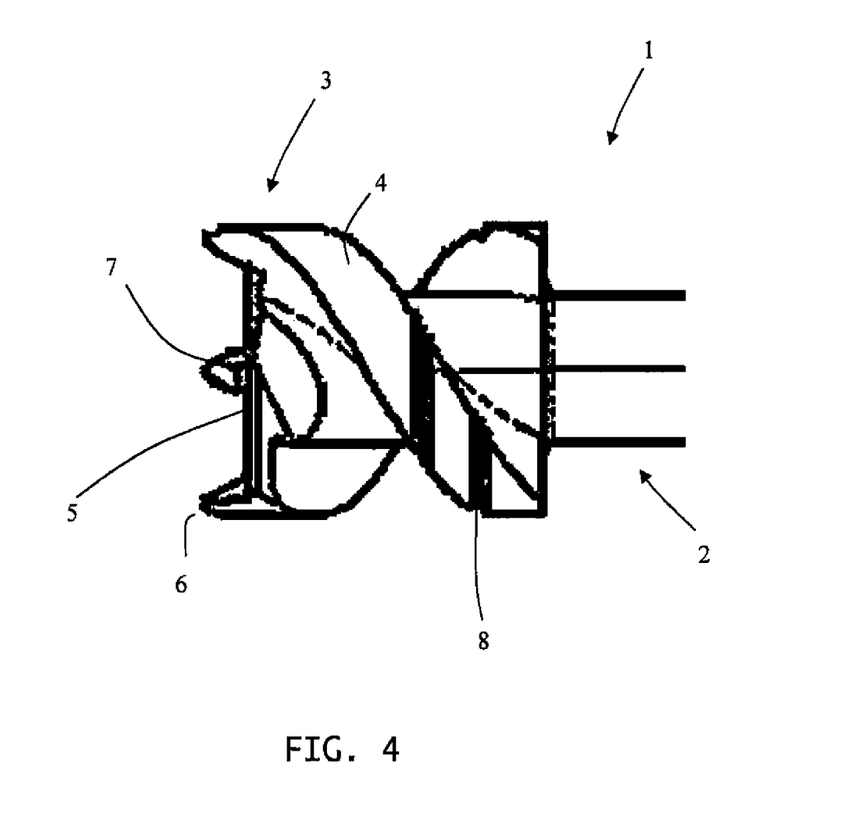
FIG. 4 is an enlarged view of the distal end of the drill of FIG. 1.

In one group of embodiments in accordance with the present invention, a drill bit with a tapered point at the distal end is employed. FIGS. 1, 2, and 4 illustrate a drill bit 1 according to such embodiments As shown in FIGS. 1, 2, and 4, a drill bit 1 comprises a longitudinal shaft 2, with a proximal end 21, a distal end 22, and a longitudinal axis 23 extending between the proximal end 21 and the distal end 22. Drill bit 1 has a cutting head 3 with at least one flute 4, cutting edge 5, offset leading spur 6, and a tapered point 7.

The drill bit 1 also has a depth controlling element that facilitates the use of the drill bit to create holes of a desired depth. In various embodiments, the depth controlling element may be in the form of visual markings 8, which may be located on the cutting head 3, proximal end 21, distal end 22 or other portion of the longitudinal shaft 2, or on the mechanical stop 9. In various embodiments, the mechanical stop 9, itself, may be a depth controlling element. In other embodiments, the depth controlling element may comprise both visual markings 8 and a mechanical stop 9.

The drill bit 1 also has a connection portion 10, providing connection between the drill bit 1 and a driving means. This connection can be a Hudson connection or another type of connection. These and other components of the drill bit 1 are each described in greater detail below.

Referring first to FIGS. 1 and 2, a drill bit 1 is depicted comprising, in general, an elongated cylindrical shaft 2 with a cutting, head 3 at the distal end 22. The shaft 2 of the drill bit 1 may be rigid or flexible. A rigid shaft may provide the benefit of strength and support, but may offer limited access to difficult locations. A flexible shaft may provide greater access to difficult locations, but may not offer the strength and support of the rigid shaft. Desirably, the drill bit 1 is made of biologically acceptable, instrument grade steel.

The cutting head 3 is generally cylindrically shaped with a diameter greater than the diameter of the adjacent portion of the shaft 2. In preferred embodiments, a portion of the shaft 2 that is adjacent and proximal to the cutting head 3 has a reduced diameter (reduced diameter portion 11) relative to the remainder of the shaft 2.

Two helical flutes 4 wrap around the cutting head 3 of the drill bit 1. However, alternatively, there may be one flute or more than two flutes. Preferably there will be no more than four flutes. Multiple flutes allow for multiple cutting edges to separate osteochondral material more quickly. However, a single flute is capable of removing chips from a hole more efficiently. Further, the helical angle of the flutes may vary. A high helical angle will allow for smoother hole walls by reducing vibration, but are not as efficient at chip removal as a low helical angle. Preferably the helical angle is greater than 45 degrees. In rotation, the flute(s) describe a path that defines the cutting diameter of the cutting head.

Referring to FIG. 4, the distal end of each flute 4 terminates at a lip which serves as a cutting edge 5 of the drill. The cutting edges 5 of the drill bit 1 may have high or low relief angles and the cutting edges 5 may extend either perpendicularly from the longitudinal axis or at an angle from the longitudinal axis 23 to the periphery of the cutting head 3.

At the periphery of the cutting edge 5 of each flute 4, away from the longitudinal axis 23 of the drill 1, is an offset leading spur 6. The spur 6 assists in precisely and clearly cutting the overlying soft tissue and may aid in stabilization of the drill bit 1. The spur 6 also provides a visualization of the perimeter of the cut before material is removed, and further confirms perpendicularity and location. The spur 6 is offset from the cutting edge 5 and extends distally from each flute 4.

At the proximal end 21 of the shaft 2 is a connection portion 10 that is used to connect the drill bit 1 to a driving means. The driving means can be powered (mechanical, electrical, pneumatic, etc.) or manual (T-handle, ratchet, etc.). The driving means imparts rotation to the drill bit 1 and may also provide axial movement to the drill bit 1.

The drill bit 1 also has a depth controlling element that facilitates the use of the drill bit to create holes of a desired depth. In various embodiments, the depth controlling element may be in the form of one or more visual markings 8, which may be located on the cutting head 3, proximal end 21, distal end 22 or other portion of the longitudinal shaft 2, or on the mechanical stop 9. In various embodiments, the mechanical stop 9, itself, may be a depth controlling element. In other embodiments, the depth controlling element may comprise both visual markings 8 and a mechanical stop 9.

When present, the visual markings 8 may be used to assess and control the depth of the drill bit 11 as it is driven into the selected osteochondral site. In practice these visual markings 8 provide information related to the distance between the visual marking 8 and a second reference point distal to the visual marking 8. In various embodiments, the second reference point may correspond to the cutting edge 5, the distal tip of the offset leading spur 6, or the distal tip of the tapered point (described below).

Desirably, these visual markings 8 include one or more grooves, preferably circumferential grooves, etched into the cutting head 3. The visual markings 8 on the cutting head 3 of the drill bit 1 are incremented through an acceptable range of hole depths as to allow for an easy method for controlling and assessing desired hole depths while drilling. In one embodiment a first mark may indicate a distance of 6 mm from the cutting edge, a second mark may indicate a distance of 8 mm from the cutting edge, and a back surface of the cutting head 3 may indicate a distance of 10 mm from the cutting edge. In various embodiments, colored material may be deposited within the grooves. Alternatively, the visual markings 8 may comprise a surface mark or band of a color contrasting with the adjacent surface of the drill bit 1. In yet other embodiments, the back of the cutting head 3 may be used to assess and control the depth of the drill bit 1.

A mechanical stop 9 may also be used, and preferably is used, to assess and control the depth that the drill bit 1 is driven into the selected osteochondral site. A mechanical stop 9 is located between the connection portion 10 and the cutting head 3. The mechanical stop 9 may be integral to, i.e., machined onto, the drill bit 1, may be attachable and/or removable, or may be movable along the length of the shaft 2.

Located at the distal end of the shaft 2, along the longitudinal axis 23, is a tapered point 7 extending distally beyond the cutting edge 5 that is used to stabilize and guide the drill bit 1 into the desired location. The tapered point 7 may, and preferably does, extend distally beyond offset leading spur 6. The tapered point 7 can be a variety of shapes. For example, as show in FIG. 4, the tapered point 7 is of a four-sided pyramidal shape, and as shown in FIG. 2, the tapered point 7 includes threads, i.e., it has a fluted or threaded exterior surface.

When the tapered point 7 is threaded it allows the drill bit 1 to be easily self-started into the selected osteochondral site without the need of a pilot hole. The threaded tapered point 7 also aids in the advancement of the drill bit 1 by pulling the drill bit 1 into the selected osteochondral site as torque is applied, reducing the need for axial force. The tapered point 7 of the drill bit 1 may be integral to, i.e., machined onto, the drill bit 1 or may be attachable and/or removable.

In operation, the drill bit 1 of FIGS. 1, 2, and 4 is used to create a hole in a selected osteochondral site. The connection portion 10 of the drill bit 1 is connected to the driving means and then the drill bit 1 is positioned so the tapered point 7 of the drill bit 1 is above the selected osteochondral site. The driving means is then activated to impart rotation to the drill bit 1, and the drill bit 1 is contacted with the osteochondral site causing the cutting edges 5 of the drill bit 1 to cut into the selected osteochondral site and create a hole. Focusing on the elements of the cutting head 3, as the drill bit 1 is advanced into the osteochondral site, the offset leading spur 6 contacts the cartilage and the cutting edge 5 contacts the bone, causing the displacement of the cartilage and bone proximally. The displaced cartilage and bone is collected in the portion of the shaft 2 having a reduced diameter (reduced diameter portion 11) relative to the remainder of the shaft 2.

The visual markings 8, the mechanical stop 9, or both can be used to determine, and thus control, the depth of the hole created. Once the desired drilling depth has been reached, rotation of the drill bit 1 is discontinued and the drill bit 1 is removed from the osteochondral site. The drill bit 1 may need to be counter-rotated prior to removal, depending on the type of tapered point 7 that is utilized.

Figure 3:
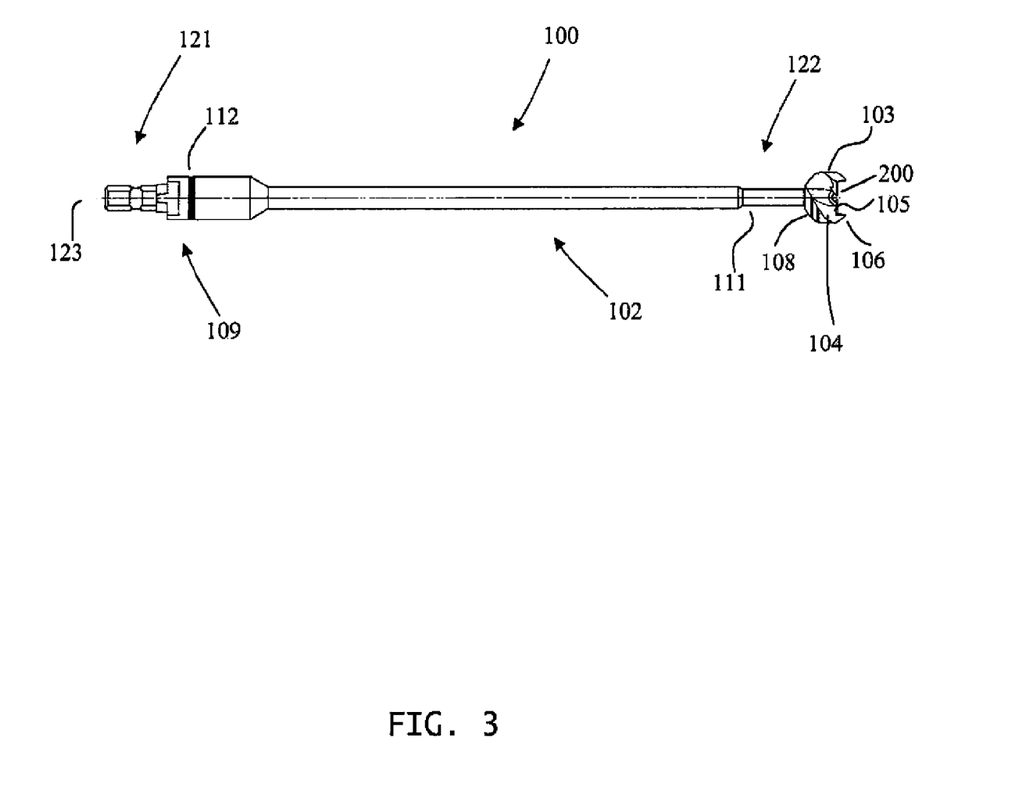
FIG. 3 is an elevational view showing a drill of the present invention with an internal bore extending along the longitudinal axis of the shaft.
Figure 5:
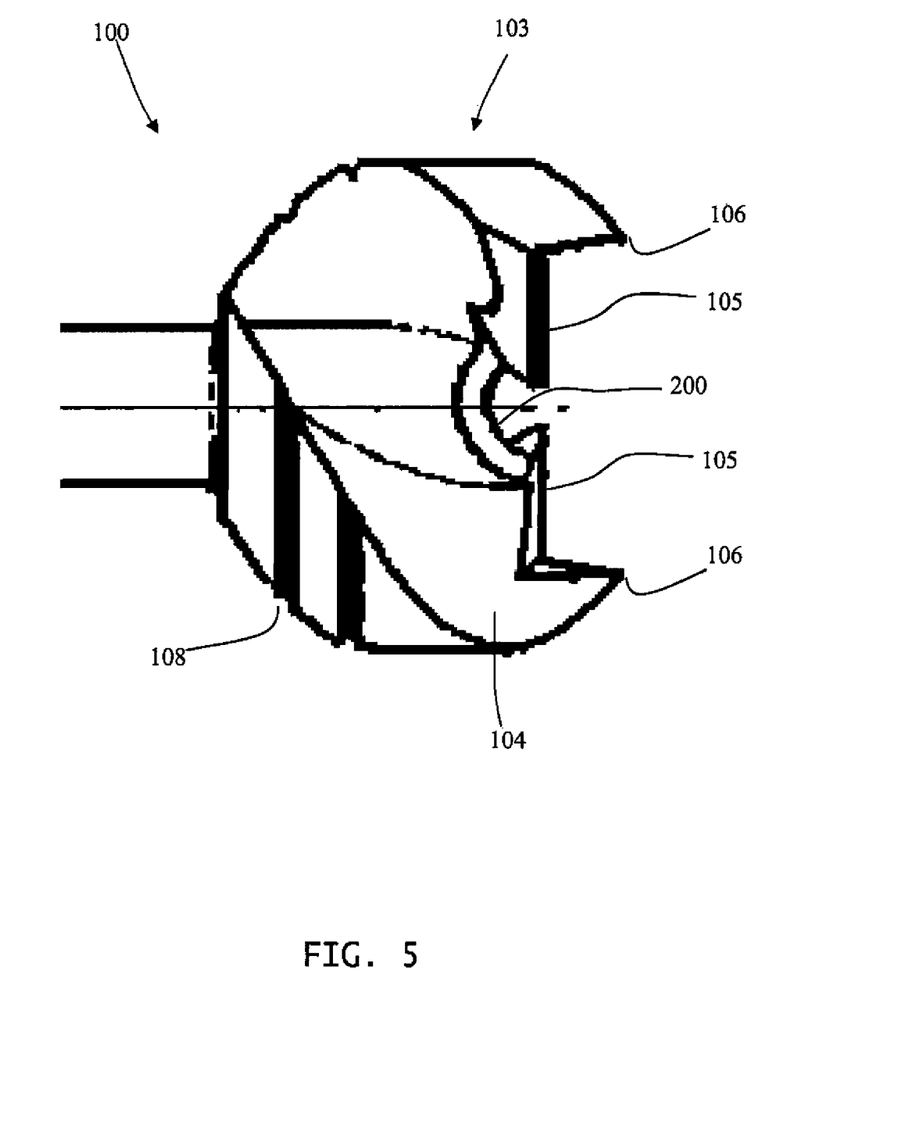
FIG. 5 is an enlarged view of the distal end of the drill of FIG. 3.

In a second group of embodiments in accordance with the present invention, a drill bit with an internal bore for receiving a guide wire is employed. FIGS. 3 and 5 illustrate a drill bit 100 according to such embodiments. The guide wire aids in the guiding of the drill bit 100 into the correct location while maintaining a desired alignment or orientation of the drill bit 100 with respect to the tissue being prepared. The guide wire may also include markings that serve as visualization means to assess and control the depth of the drill bit 100.

Similar to FIGS. 1 and 2, the drill bit 100 of FIG. 3 comprises, in general, an elongated cylindrical shaft 102, with a proximal end 121, a distal end 122, and a longitudinal axis 123 extending between the proximal end 121 and the distal end 122. The drill bit 100 of FIG. 3 includes an internal bore 200 extending along the longitudinal axis 123 of the shaft 102 adapted to receive a guide wire. Desirably, the drill bit 100 and the guide wire are made of biologically acceptable, instrument grade steel.

Drill bit 100 has a cutting head 103 at its distal end 122. Rather than, or in some embodiments in addition to, using a tapered and/or threaded point, drill bit 100 of FIG. 3 utilizes a guide wire to stabilize and guide the drill bit 100 to the correct location.

Similar to drill bit 1 described above with reference to FIGS. 1, 2, and 4, the drill bit 100, referring to FIGS. 3 and 5, has a cutting head 103 with at least one flute 104, cutting edge 105, and offset leading spur 106. The drill bit 100 also has a depth controlling element that facilitates the use of the drill bit to create holes of a desired depth. In various embodiments, the depth controlling element may be in the form of visual markings 108, which may be located on the cutting head 103, proximal end 121, distal end 122 or other portion of the longitudinal shaft 102, or on the mechanical stop 109. In various embodiments, the mechanical stop 109, itself, may be a depth controlling element. In other embodiments, the depth controlling element may comprise both visual markings 108 and mechanical stop 109. Markings on the guide wire can also serve as depth controlling means. In preferred embodiments, a portion of the shaft 102 that is adjacent and proximal to the cutting head 103 has a reduced diameter (reduced diameter portion 111) relative to the remainder of the shaft 102. As these features of drill bit 100 are similar to corresponding features of drill bit 1, they are not described in great detail here.

Drill bit 100 of FIG. 3 is used in conjunction with a guide wire and/or threaded point that has been previously inserted into a selected osteochondral site. The guide wire is inserted using a power drill, a surgical hammer, or another method. In operation, the connection portion 110 of drill bit 100 is connected to the driving means and then positioned over the guide wire so that the distal end of drill bit 100 is in contact with or slightly above the selected osteochondral site. The driving means is then activated to impart rotation to the drill bit 100. Rotating and in contact with the osteochondral site, the cutting edges 105 of the drill bit 100 cut into the selected osteochondral site and create a hole. Focusing on the elements of the cutting head 103, as the drill bit 100 is advanced into the osteochondral site, the offset leading spur 106 contacts the cartilage and the cutting edge 105 contacts the bone, causing the displacement of the cartilage and bone proximally. The displaced cartilage and bone is collected in the portion of the shaft 102 having a reduced diameter (reduced diameter portion 111) relative to the remainder of the shaft 102.

The visual markings 108, the mechanical stop 109, markings on the guide wire, or any combination of the aforementioned can be used to determine, and thus control, the depth of the hole created. Once the desired drilling depth has been reached, rotation of the drill bit 100 is discontinued and the drill bit is removed from the osteochondral site.

Desirably, drill bit 1 and chill bit 100 will have a marking indicating the cutting diameter of the cutting head 3 and 103. The marking indicating the cutting diameter may be comprised of a colored band 12 and 112 located on the mechanical stop of the drill bit. This colored marking allows a user to easily identify the cutting diameter of the drill bit. In alternative embodiments, the marking indicating the cutting diameter of the cutting head 3 and 103 may be provided by other means. For example, the drill bit may be marked with an actual numerical indication of the cutting diameter, a part number corresponding to the cutting diameter, or other etching or pattern corresponding to the cutting diameter.

In various embodiments, the drill bits 1 and 100 of the present invention may be used in conjunction with a cannulated instrument that assists in guiding the drill bit 1 and 100 to the desired location and protecting tissues adjacent or in proximity to the site to be prepared. The cannulated instrument can take many forms, including a hollow cylinder or a punch with a sharpened rim. The cannulated instrument can be used to interface with a mechanical stop 9 and 109 on the drill bit 1 and drill bit 100 to control the drilling depth and/or used to contain or remove tissue particulate. Additionally, the cannulated instrument can be used in combination with the reduced diameter portion of the shaft (reduced diameter portion 11 and 111) to contain tissue particulates and/or used in combination with the flutes 4 and 104 or rake angles to propel tissue particulates proximally. The cannulated instrument can also be used in conjunction with an obturator that allows a user to navigate through soft tissue without damage to the tissue and seat the cannula against the desired osteochondral site. In such instances, the obturator is removed from the cannulated instrument before drill bit 1 or drill bit 100 is inserted into the cannulated instrument. Preferably, drill bit 1 and drill bit 100 are used without a cannulated instrument and any associated obturator.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Whenever a numerical range with a lower limit and an upper limit is disclosed, any number falling within the range is specifically disclosed. Moreover, the indefinite articles "a" or "an", as used in the claims, are defined herein to mean one or more than one of the element that it introduces.

What is claimed is:

1. A drill bit comprising:
    a shaft having a proximal end, a distal end, and a longitudinal axis extending between the proximal end and the distal end;
    a cutting head located at the distal end of the shaft and having at least one helical flute, wherein a maximum diameter as defined by outer surfaces of the at least one helical flute is the same at a proximal-most region and a distal-most region of the cutting head, wherein the cutting head further includes a cutting edge and an offset leading spur, the at least one helical flute defining a helical angle of at least 45 degrees with the longitudinal axis of the shaft, the offset leading spur defining a first cutting diameter that is equivalent to a second cutting diameter defined by the cutting edge;
    a tapered point located along the longitudinal axis at a distal end of the cutting head for guiding the drill bit; and
    wherein a portion of the shaft located adjacent and proximal to the cutting head has a reduced diameter relative to the remainder of the shaft.

2. The drill bit of claim 1, wherein the tapered point is threaded.

3. The drill bit of claim 1, wherein the shaft is flexible.

4. The drill bit of claim 1, further comprising a depth controlling element.

5. The drill bit of claim 4, wherein the depth controlling element comprises one or more visual markings located on the cutting head, a mechanical stop located proximal to the cutting head, or a combination thereof.

6. The drill bit of claim 5, wherein the one or more visual markings are etched into the cutting head.

7. The drill bit of claim 5, wherein the mechanical stop is fixed.

8. The drill bit of claim 5, wherein the mechanical stop is removable.

9. The drill bit of claim 1, further compromising a marking indicating the first and second cutting diameters of the cutting head.

10. The drill bit of claim 9, wherein the marking indicating the first and second cutting diameters of the cutting head comprises a colored band located on a mechanical stop that is located proximal to the cutting head.

11. A method for creating a hole in a selected osteochondral site using a drill bit:

the drill bit comprising:
a shaft having a proximal end, a distal end, and a longitudinal axis extending between the proximal end and the distal end;
a cutting head located at the distal end of the shaft and having at least one helical flute, wherein a maximum diameter as defined by outer surfaces of the at least one helical flute is the same at a proximal-most region and a distal-most region of the cutting head, wherein the cutting head further includes a cutting edge and an offset leading spur, the at least one helical flute defining a helical angle of at least 45 degrees with the longitudinal axis of the shaft, the offset leading spur defining a first cutting diameter that is equivalent to a second cutting diameter defined by the cutting edge;
a tapered point located along the longitudinal axis at a distal end of the cutting head for guiding the drill bit;
and wherein a portion of the shaft located adjacent and proximal to the cutting head has a reduced diameter relative to the remainder of the shaft;
the method comprising:
advancing the drill bit into the selected osteochondral site;
contacting cartilage with the offset leading spur;
contacting bone with the cutting edge;
displacing cartilage and bone proximally; and
collecting displaced cartilage and bone in the portion of the shaft having a reduced diameter relative to the remainder of the shaft.

12. The method of claim 11, further comprising using a tapered point of the drill bit to guide the path of the drill bit.

13. The method of claim 11, further comprising using a cannula to guide the path of the drill bit.

14. The method of claim 13, further comprising using the cannula and the portion of the shaft having a reduced diameter relative to the remainder of the shaft to contain bone and cartilage.

15. The method of claim 11, further comprising using a depth controlling element to achieve a desired drilling depth.

16. The drill bit of claim 15, wherein the depth controlling element comprises one or more visual markings located on the cutting head, a mechanical stop located proximal to the cutting head, or a combination thereof.

17. A drill bit comprising:
a shaft having a proximal end, a distal end, and a longitudinal axis extending between the proximal end and the distal end;
a cutting head located at the distal end of the shaft and having at least one helical flute, wherein a maximum diameter as defined by outer surfaces of the at least one helical flute is the same at a proximal-most region and a distal-most region of the cutting head, wherein the cutting head further includes a cutting edge and an offset leading spur, the offset leading spur defining a first cutting diameter that is equivalent to a second cutting diameter defined by the cutting edge;
a tapered point located along the longitudinal axis at a distal end of the cutting head for guiding the drill bit, the tapered point including a threaded exterior surface;
a mechanical stop located proximal to the cutting head and at least partially surrounding the shaft, the mechanical stop movable along the longitudinal axis of the shaft to adjust a maximum cutting depth; and
wherein a portion of the shaft located adjacent and proximal to the cutting head has a reduced diameter relative to the remainder of the shaft.

18. The drill bit of claim 17, wherein a distal end of the tapered point defines a pyramidal shape.

19. The drill bit of claim 18, wherein the pyramidal shape is a four-sided pyramidal shape.

20. The drill bit of claim 19, wherein the tapered point is removable from the cutting head.

21. The drill bit of claim 20, wherein the at least one helical flute defines a helical angle of at least 45 degrees with the longitudinal axis of the shaft.

* * * * *